United States Patent
Morris

(10) Patent No.: US 12,161,790 B2
(45) Date of Patent: Dec. 10, 2024

(54) PERITONEAL DIALYSIS (PD) CATHETER WEIGHTED ANCHOR

(71) Applicant: The University of Vermont and State Agricultural College, Burlington, VT (US)

(72) Inventor: Christopher S. Morris, South Hero, VT (US)

(73) Assignee: The University of Vermont and State Agricultural College, Burlington, VT (US)

( * ) Notice: Subject to any disclaimer, the term of this patent is extended or adjusted under 35 U.S.C. 154(b) by 1183 days.

(21) Appl. No.: 16/623,313

(22) PCT Filed: Jun. 14, 2018

(86) PCT No.: PCT/US2018/037648
§ 371 (c)(1),
(2) Date: Dec. 16, 2019

(87) PCT Pub. No.: WO2018/232190
PCT Pub. Date: Dec. 20, 2018

(65) Prior Publication Data
US 2020/0206469 A1    Jul. 2, 2020

Related U.S. Application Data

(60) Provisional application No. 62/519,568, filed on Jun. 14, 2017.

(51) Int. Cl.
*A61M 1/28* (2006.01)
*A61L 29/02* (2006.01)
*A61L 29/14* (2006.01)
*A61M 25/00* (2006.01)
*A61M 25/04* (2006.01)

(52) U.S. Cl.
CPC ............. *A61M 1/285* (2013.01); *A61L 29/02* (2013.01); *A61L 29/14* (2013.01); *A61M 25/005* (2013.01); *A61M 25/04* (2013.01)

(58) Field of Classification Search
CPC .... A61M 1/285; A61M 25/005; A61M 25/04; A61L 29/02; A61L 29/14
See application file for complete search history.

(56) References Cited

U.S. PATENT DOCUMENTS

| | | | | |
|---|---|---|---|---|
| 3,155,097 A * | 11/1964 | Barron | ................ | A61J 15/0003 604/270 |
| 4,410,320 A * | 10/1983 | Dykstra | .............. | A61J 15/0003 604/270 |
| 4,654,036 A * | 3/1987 | Tolkoff | .................... | A61J 15/00 604/27 |
| 2003/0004520 A1 * | 1/2003 | Haarala | ............. | A61M 39/0247 606/108 |

* cited by examiner

*Primary Examiner* — Brandy S Lee
(74) *Attorney, Agent, or Firm* — Hodgson Russ LLP

(57) ABSTRACT

The present invention has to do with a method and system for peritoneal dialysis catheter weighted anchors. The peritoneal dialysis catheter weighted anchors can be inserted and retrieved using standard techniques and available insertion/retrieval systems. The peritoneal dialysis catheter weighted anchors can be attached and secured to all types of PD catheters as an ancillary anchor device.

18 Claims, 4 Drawing Sheets

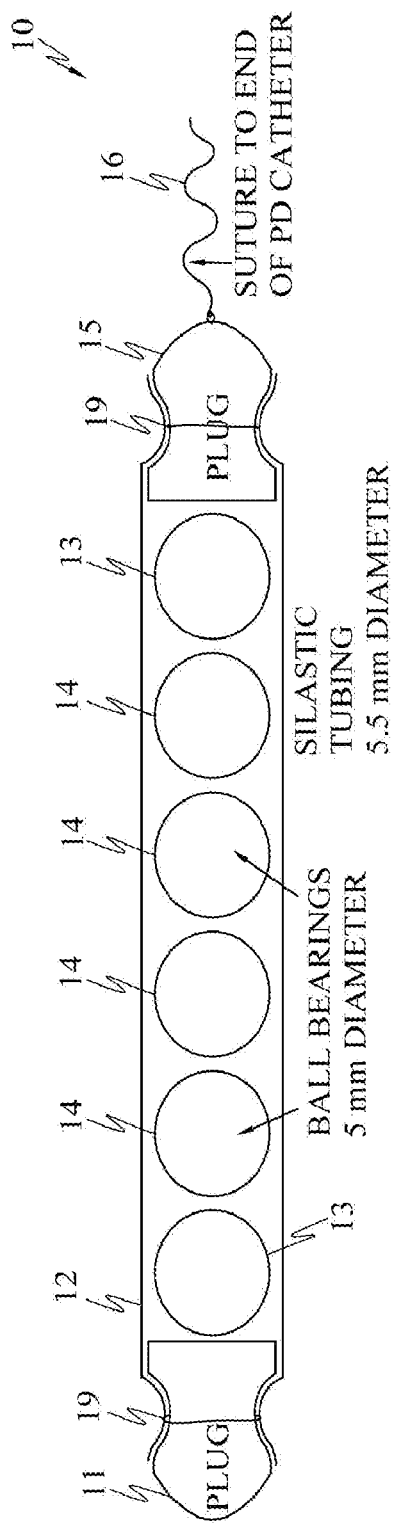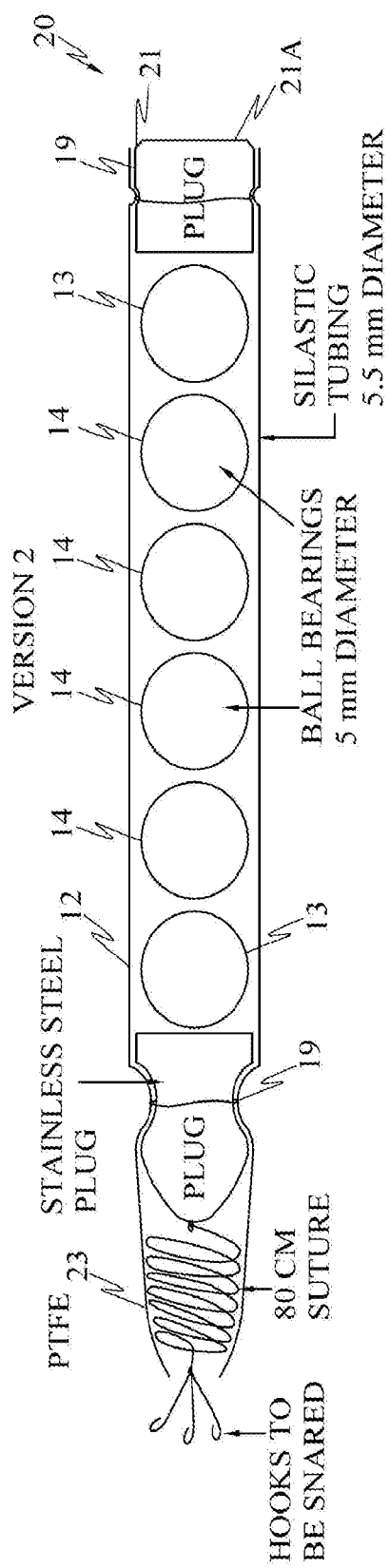
FIG. 1
FIG. 2

PERITONEAL DIALYSIS (PD) CATHETER WEIGHTED ANCHOR

CROSS-REFERENCE TO RELATED APPLICATIONS

The present application is related to, claims the earliest available effective filing date(s) from (e.g., claims earliest available priority dates for other than provisional patent applications; claims benefits under 35 USC § 119(e) for provisional patent applications), and incorporates by reference in its entirety all subject matter of the following listed application(s) (the "Related Applications") to the extent such subject matter is not inconsistent herewith; the present application also claims the earliest available effective filing date(s) from, and also incorporates by reference in its entirety all subject matter of any and all parent, grandparent, great-grandparent, etc. applications of the Related Application(s) to the extent such subject matter is not inconsistent herewith:

U.S. provisional patent application 62/519,568, entitled "Peritoneal Dialysis Catheter Weighted Anchor", naming Christopher S. Morris as inventor, filed 14 Jun. 2017.

BACKGROUND

1. Field of Use

The present invention relates to a catheter, particularly intended for use with peritoneal dialysis. In particular, the invention relates to a peritoneal dialysis catheter suitable to prevent significant catheter migration.

2. Description of Prior Art (Background)

Peritoneal dialysis (PD) catheters are used to infuse and drain dialysate fluid within the peritoneal space of the abdomen. The dialysate fluid removes substances across the peritoneal membrane through passive diffusion in patients with impaired or no renal function.

PD catheters work best when the distal (active) end is located within the most dependent portion of the peritoneal space, which is in the posterior part of the inferior pelvis, known as the pouch of Douglas (cul de sac) in women, and the recto-vesico pouch (cul de sac) in men.

Unfortunately, PD catheters have a propensity to migrate or float out of the pelvis due to distention of the abdomen and pelvis with fluid during PD, movement or repositioning of the patient, or bowel peristalsis. A large percentage of malfunctioning PD catheters have been found to have migrated out of the cul de sac of the pelvis. This dislocation of the PD catheter may cause inefficient dialysis, compromise of drainage of the dialysate due to poor outflow from omental wrap, pain on filling, and intolerance of PD. Dislocation is one the most common causes of PD catheter failure and removal.

Not only are an increasing number of patients developing chronic kidney failure, but a larger percentage of kidney failure patients choose PD over hemodialysis. PD can be performed at home and at night, when the patient is sleeping. PD is more cost effective and may cause less of a shock to the body than hemodialysis, and therefore many patients feel better on PD than on hemodialysis. The number of patients on PD is predicted to rise in the future.

Currently, no commercially available device exists in the U.S. to percutaneously fix a PD catheter to the cul de sac of the pelvis. A case report of using a surgically placed testicular prosthesis attached to the distal end of the catheter, which applied weight to the distal catheter end to stabilize it, exists, but the technique requires surgical insertion and is not commercially available.

In 1994, Di Paolo developed and patented a weighted tip of a Tenckhoff straight PD catheter using a 12 gram cylinder of tungsten fixed within the tip of the catheter.

The so-called Tenckhoff-catheter can be of the straight type or the spiral-shaped type. This catheter consists of a silicon tube, on to which are fastened one or two Dacron cuffs, to which peritoneal fibers may grow attached, thereby helping to fix, to some degree, the catheter in position after surgical implantation.

One problem with this catheter is that the holes in the catheter can be blocked during the outward-feed phase, due to the effect of the suction pressure. During the inward-feed phase, too high flows can lead to the catheter moving in the peritoneal cavity. The force which occurs when the fluid flows out causes the tip of the catheter to lash about and to be displaced when the flow is initiated. This catheter migration is one of the reasons for a catheter having to be changed. This movement can also affect the peritoneal membrane's susceptibility to infection.

With a straight catheter for peritoneal dialysis having an open distal end, a large part of the total flow, as much as two-thirds, will pass out through the tip opening. High outflow speeds thereby result, which could damage the fibers in the peritoneum. Additionally, the force which acts on the tip of the catheter due to the outflow of fluid in an axial direction becomes excessively high. It is this force which causes the catheter to lash about and be displaced when the flow is initiated. It is desirable to reduce, or eliminate, displacement of the catheter, particularly at higher outward-feed flows.

BRIEF SUMMARY

The foregoing and other problems are overcome, and other advantages are realized, in accordance with the presently preferred embodiments of these teachings.

The present invention can be used percutaneously, as well as an adjunct to laparoscopic, or surgically inserted devices (straight or curled), obviating the need to extend the surgical field into the pelvis. A technical dilemma of placing weights that are too large to pass through a side hole directly is resolved by the invention. A proprietary weight sleeve, used to anchor the distal coiled (active) end of the catheter, is placed through the lumen of the 18 French peel away insertion sheath, ahead of and immediately adjacent to the PD catheter, as both are pushed into the cul de sac. The weight sleeve is flexible, so that it conforms to the shape of the cul de sac. The design of the weight sleeve will allow weight much greater than 12 grams to be used to anchor the PD catheter.

The present invention serves to temporarily fasten the distal (active) end of a peritoneal dialysis catheter within the cul de sac of the pelvis. This system will prevent the catheter from becoming displaced out of the cul de sac of the pelvis and will allow it to function normally. It can also be removed percutaneously.

In accordance with one embodiment of the present invention a weighted peritoneal dialysis (PD) catheter anchor is provided. The PD catheter anchor includes a watertight weight sleeve having distal ends and at least two plugs, each affixable to each of the distal ends to form a watertight chamber within the watertight sleeve. The PD anchor also includes a plurality of outer weights enclosed within the watertight chamber.

The invention is also directed towards a peritoneal dialysis (PD) catheter that includes a weighted PD anchor. The weighted PD anchor includes a watertight sleeve having distal ends and at least two plugs affixable to each of the distal ends of the watertight weight sleeve to form a watertight chamber within the watertight sleeve. The PD anchor also includes a plurality of outer weights enclosed within the watertight chamber and form an internal watertight chamber between the plurality of outer weights. Within the internal watertight chamber is at least on inner weight.

Yet, another embodiment of the invention includes A weighted peritoneal dialysis (PD) catheter anchor having a watertight sleeve having distal ends. The watertight sleeve is a medical grade silicone tubing and has at least two plugs, each affixable to each of the distal ends of the watertight weight sleeve to form a watertight chamber within the watertight sleeve. The plugs are biologically inert material and may be manufactured from stainless steel, titanium, or medical grade polymers. The PD anchor also includes a plurality of outer weights, enclosed within the watertight chamber and form an internal watertight chamber between the plurality of outer weights. The plurality of outer weights each are stainless steel weights. The PD anchor also includes at least one inner weight, wherein the at least one inner weight is disposed between the plurality of outer weights in the internal watertight chamber. The inner weights are manufactured from a biologically inert material such as stainless steel, titanium, or tungsten.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIG. 1 is a pictorial illustration of the weighted peritoneal dialysis catheter anchor in accordance with the present invention;

FIG. 2 is a pictorial illustration of an alternate weighted peritoneal dialysis catheter anchor in accordance with the present invention shown in FIG. 1;

DETAILED DESCRIPTION

Figure 2A:
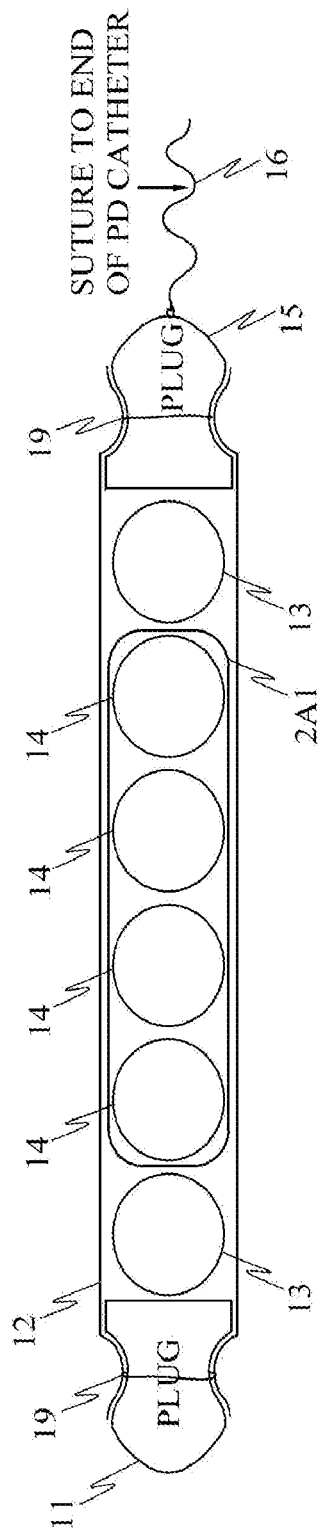
FIG. 2A is a pictorial illustration of the weighted peritoneal dialysis catheter anchor illustrating an inner weight sleeve in accordance with the present invention shown in FIG. 1.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example; and If the specification states a component or feature "may," "can," "could," "should," "preferably," "possibly," "typically," "optionally," "for example," or "might" (or other such language) be included or have a characteristic, that particular component or feature is not required to be included or to have the characteristic.

Referring now to FIG. 1 there is shown a pictorial illustration of the weighted peritoneal dialysis catheter anchor 10 in accordance with the present invention. The weight sleeve 10 consists of a row or series of metallic ball bearings 13, 14 encased in a water tight casing 12 made of a medical grade polymer or silicon material such as, for example, SILASTIC tubing, thin walled polytetrafluoroethylene (PTFE), or a combination of materials. The weight sleeve 10 is impervious and sterilized. The ball bearings 13 at either end of tubing 12 may be stainless steel, or any suitable material, and over sewn with suture material to ensure that the entire system is water tight.

Although both tungsten and stainless steel are considered to be biologically inert, there is a small chance that tungsten can interfere with iron metabolism. Therefore, the peritoneal dialysis catheter weighted anchor 10 or 20 designed to isolate the tungsten ball bearings 14 from any possible interaction with body fluids. The stainless-steel ball bearings 13, acting as a cap on each end of the device, as well as the prolene sutures 19 crimping off each end of the device 10 or 20, functioned to isolated the tungsten balls from exposure to body fluids, Only the stainless-steel ball bearings 13 at either end of the water tight casing 12 have any potential of contacting body fluids while resting in the peritoneal space.

The ball bearings 13 are may be any suitable material, such as stainless steel, 316 surgical stainless steel, or another heavier metal. Multiple ball bearings are used, as necessary. The weight within the weight sleeve 10 or 20 could also be made from weights of varying lengths, diameters, and suitable compositions.

The length of the weight sleeve 10 depends on the amount of weight necessary for the anchor to be effective. Therefore, any desired amount of weights can be placed into the weight sleeve 10 or 20 to serve as the weighted anchor. The weight sleeve 10 is flexible, allowing it to conform to the shape of the cul de sac, or even to form a coil within the cul de sac of the pelvis.

To further ensure weights which may or may not be biologically inert ball bearings 14 can be further isolated within an inner sheath. See FIG. 2A: 2A1. This allows for fewer heavier weights which may not be biologically inert but can keep the size of the weight sleeve 10 or 20 smaller which may be more suitable depending on the patient and location of the weight sleeve 10 or 20.

Figure 3:
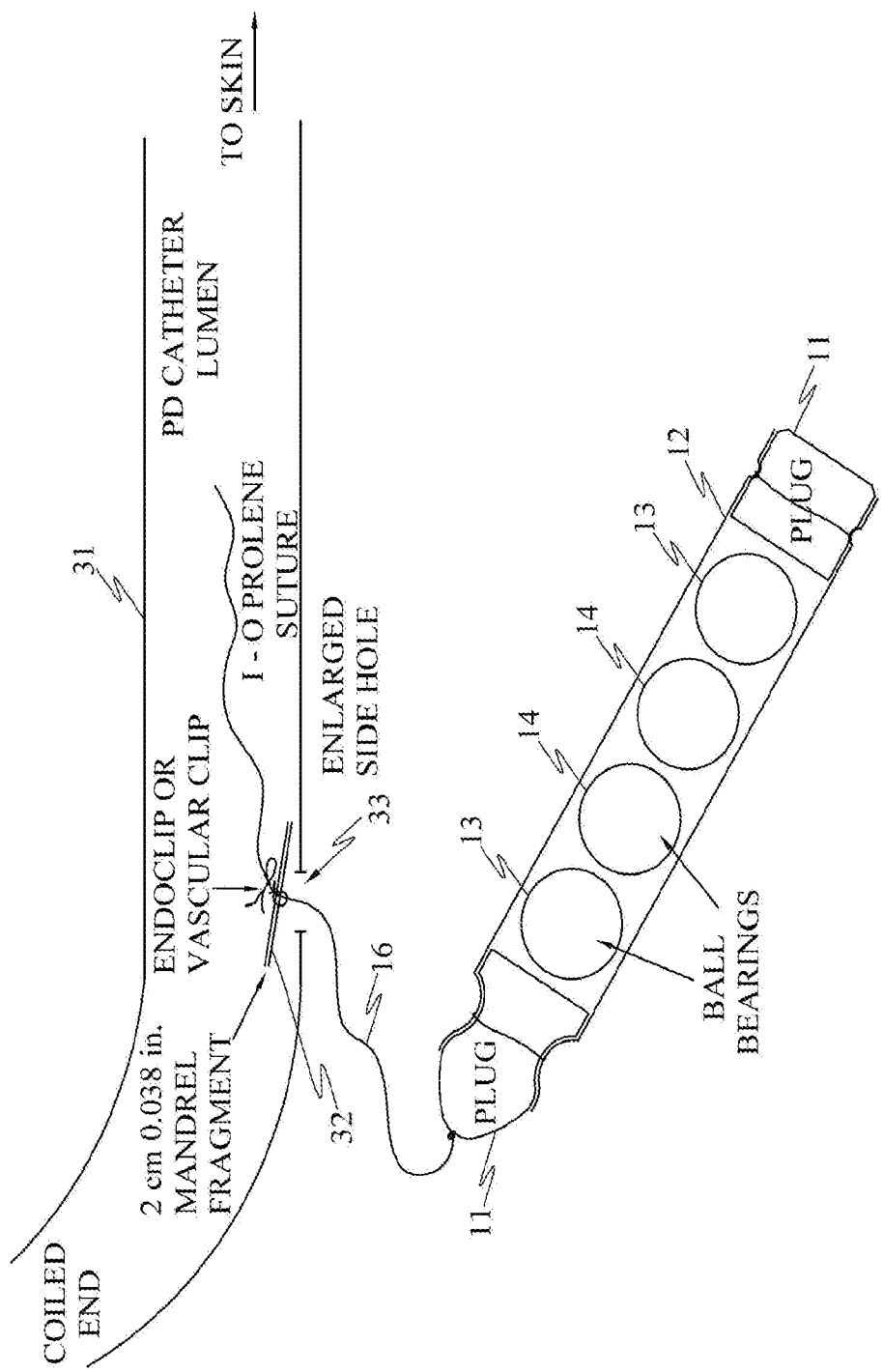
FIG. 3 is a pictorial illustration of a catheter weighted in accordance with the invention shown in FIG. 1 or FIG. 2.

The SILASTIC tubing 12 can be pre-shaped into a coil with the use of heat and retains thermal memory. The ends of the tubing 12 of the weight sleeve are enclosed with water tight plugs 11, 15. The metallic plugs 11, 15 may be any suitable biologically inert material, such as, for example, stainless steel, titanium, tungsten or bioinert polymers. The weight sleeve 10 is inserted into the cul de sac prior to placing the PD catheter as shown in FIG. 3.

In one embodiment, the end of the trailing plug 15 is constricted, which allows a 5 to 10 cm length of non-absorbable suture (1-0 or heavier) 16 to tie it to the end (tip) of the PD catheter (not shown). An 18 French peel away sheath (not shown) is inserted into the cul de sac, the weight sleeve 10 is advanced into the French peel away sheath. The weight sleeve 10 is attached to the leading end of the curled PD catheter, which is inserted into the French peel away sheath behind the weight sleeve 10 or 20.

A pusher rod is advanced through the PD catheter so that it rests against the weight sleeve. The entire combination of the weight sleeve, PD catheter, and pusher rod are then advanced through the French peel away sheath until the pusher rod is near the end of the peel away sheath. At this point, the weight sleeve is completely resting within the cul de sac. Finally, the PD catheter is advanced through the peel away sheath to enter the cul de sac, while holding the pusher rod stationary.

The 5 to 10 cm length of the suture 16 attaching the weight sleeve 10 to the PD catheter allows room for the curled end of the PD catheter to form. Once the PD catheter is placed into the cul de sac, no further manipulation of the weight sleeve 10 or 20 is required.

Referring also to FIG. 2 there is shown a pictorial illustration of an alternate weighted peritoneal dialysis catheter anchor 20 in accordance with the present invention shown in FIG. 1. The trailing plug 21 has a flat surface 21A which allows it to be pushed with a pushing rod. The leading-edge plug 25 is constricted, to allow a short segment of PTFE graft tubing 23 to be tied to it. Before tying the PTFE graft tubing 23 to the leading edge plug 25, an 80 cm long segment of strong (1-0 or heavier) non absorbable suture 24 is tied to the plug 25 and SILASTIC tubing 12 of the weight sleeve 20. The suture 24 is coiled and stored in the PTFE graft tubing 23.

Multiple metallic retrieval hooks 22 are tied to the leading end of the suture 24 and lightly contained within the PTFE graft tubing 23, so that they can be easily deployed from the graft tubing 23.

Referring also to FIG. 3. Once the weight sleeve 10 and PD catheter lumen 31 are in optimal positions within the cul de sac of the pelvis (not shown), the French peel away sheath is withdrawn enough to expose one of the several custom enlarged proximal side holes 33. These one mm in diameter holes 33 could be enlarged to 2 mm in diameter with a hole punch.

A French angled angiographic sheath is used to cannulate the enlarged side hole. Ideally, the French sheath is pre-loaded into the side hole 33 prior to advancing down the French peel away sheath.

Next, a French angled angiographic catheter and nitinol loop snare combination are advanced through the sheath and used to grasp a suture 16 or hook 22 of the weight sleeve resting within the cul de sac, using standard loop snare technique. The hook 22 and suture 24 is withdrawn out of the weight sleeve, pulled back into the PD catheter, and out of the back end of the PD catheter (PD catheter not shown).

Tension is applied to the suture 16 or 24 to effectively weight the curled end of the PD catheter snugly into the cul de sac. The excess suture 16 or 24 is pulled out of the PD catheter. The suture 16 or 24 is independently fixed within the lumen 31 of the PD catheter by first applying a sliding T tack and crimping a vascular clip or endoclip 32 behind it and onto the suture.

The excess suture 16 or 24 within the PD catheter is cut with a long pair of scissors (Metzenbaum scissors). This essentially provides traction to the "neck" of the curled end of the PD catheter, rather than the tip of the curled end, ensuring that the curl retains its shape. This invention solves the problem of remotely securing a T-tack suture to the inside of the distal lumen of a PD catheter.

Removing the PD catheter and attached weight sleeve 10 or 20 is accomplished in the usual manner. Once the extra catheter suture is visualized at the peritoneal insertion site, the PD catheter is removed. Then, the weight sleeve unit is pulled out of the peritoneal space.

Figure 4:
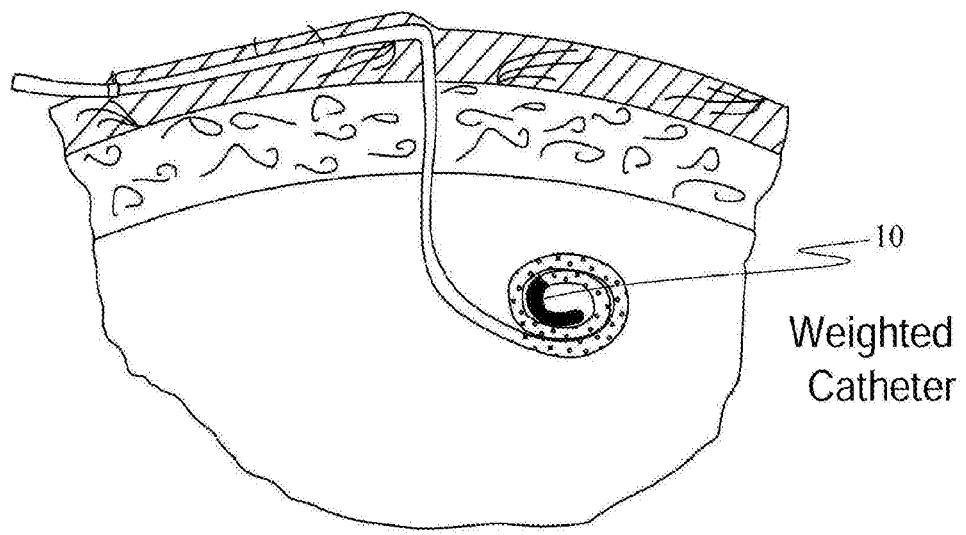
FIG. 4 is a is a pictorial illustration of a weighted PD catheter accordance with the invention shown in FIG. 1 or FIG. 2.
Figure 5:
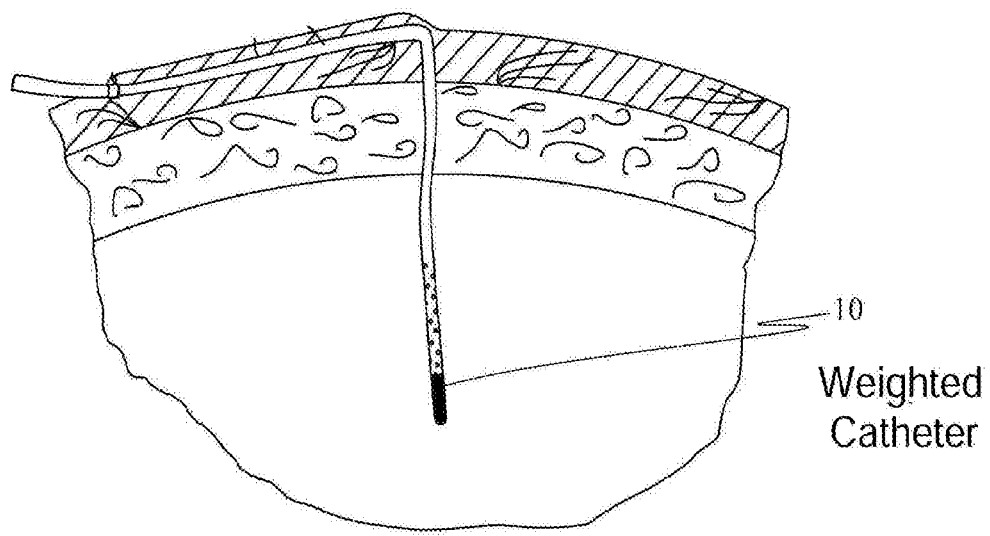
FIG. 5 is a is a pictorial illustration of an alternate weighted PD catheter accordance with the invention shown in FIG. 1 or FIG. 2.

It should be understood that the foregoing description is only illustrative of the invention. Thus, various alternatives and modifications can be devised by those skilled in the art without departing from the invention. For example, the weighted anchor 10 or 20 can be an integral portion of the PD catheter (see FIG. 4 and FIG. 5.) Accordingly, the present invention is intended to embrace all such alternatives, modifications and variances that fall within the scope of the appended claims.

What is claimed is:

1. A weighted peritoneal dialysis (PD) catheter anchor comprising:
    a watertight weight sleeve having distal ends;
    at least two plugs, each affixable to each of the distal ends to form a watertight chamber within the watertight sleeve;
    a plurality of outer weights, wherein the plurality of outer weights are enclosed within the watertight chamber; and
    an inner sheath for biologically isolating the at least one inner weight.

2. The weighted PD catheter anchor as in claim 1 wherein the watertight sleeve comprises medical grade silicone tubing.

3. The weighted PD catheter anchor as in claim 1 wherein the plugs comprise biologically inert material selected from the group consisting of stainless steel, titanium, or medical grade polymers.

4. The weighted PD catheter anchor as in claim 1 wherein the plurality of outer weights each comprise stainless steel weights.

5. The weighted PD catheter anchor as in claim 4 further comprising at least one inner weight disposed between the plurality of outer weights.

6. The weighted PD catheter anchor as in claim 5 wherein the at least one inner weight comprises a biologically inert material selected from the group consisting of stainless steel, titanium, or tungsten.

7. The weighted PD catheter anchor as in claim 5 further comprising an inner sheath for biologically isolating the at least one inner weight.

8. The weighted PD catheter anchor as in claim 1 further comprising an anchoring suture.

9. The weighted PD catheter anchor as in claim 8 wherein the anchoring suture comprises at least one hook.

10. A peritoneal dialysis (PD) catheter comprising:
    a weighted anchor, wherein the weighted anchor comprises:
        a watertight sleeve having distal ends;
        at least two plugs, each affixable to each of the distal ends of the watertight weight sleeve to form a watertight chamber within the watertight sleeve;
        a plurality of outer weights, wherein the plurality of outer weights are enclosed within the watertight chamber and form an internal watertight chamber between the plurality of outer weights;

at least one inner weight, wherein the at least one inner weight is disposed between the plurality of outer weights in the internal watertight chamber; and an inner sheath for biologically isolating the at least one inner weight.

11. The PD catheter as in claim 10 wherein the watertight sleeve comprises medical grade silicone tubing.

12. The PD catheter as in claim 10 wherein the plugs comprise biologically inert material selected from the group consisting of stainless steel, titanium, or medical grade polymers.

13. The PD catheter as in claim 10 wherein the plurality of outer weights each comprise stainless steel weights.

14. The PD catheter as in claim 10 wherein the at least one inner weight comprises a biologically inert material selected from the group consisting of stainless steel, titanium, or tungsten.

15. A weighted peritoneal dialysis (PD) catheter anchor comprising:

a watertight sleeve having distal ends, wherein the watertight sleeve comprises medical grade silicone tubing;

at least two plugs, each affixable to each of the distal ends of the watertight weight sleeve to form a watertight chamber within the watertight sleeve, wherein the plugs comprise biologically inert material selected from the group consisting of stainless steel, titanium, or medical grade polymers;

a plurality of outer weights, wherein the plurality of outer weights are enclosed within the watertight chamber and form an internal watertight chamber between the plurality of outer weights, wherein the plurality of outer weights each comprise stainless steel weights;

at least one inner weight, wherein the at least one inner weight is disposed between the plurality of outer weights in the internal watertight chamber, and wherein the at least one inner weight comprises a biologically inert material selected from the group consisting of stainless steel, titanium, or tungsten; and an inner sheath for biologically isolating the at least one inner weight.

16. The weighted PD catheter anchor as in claim 15 further comprising an anchoring suture.

17. The weighted PD catheter anchor as in claim 16 wherein the anchoring suture comprises at least one hook.

18. A weighted peritoneal dialysis (PD) catheter anchor comprising:

a watertight weight sleeve having distal ends;

at least two plugs, each affixable to each of the distal ends to form a watertight chamber within the watertight sleeve;

a plurality of outer weights, wherein the plurality of outer weights are enclosed within the watertight chamber; and an anchoring suture.

\* \* \* \* \*